US012673166B2

(12) United States Patent
Shabudin

(10) Patent No.: US 12,673,166 B2
(45) Date of Patent: Jul. 7, 2026

(54) SAFETY SYRINGE

(71) Applicant: OWEN MUMFORD LTD, Woodstock (GB)

(72) Inventor: Tahir Shabudin, Woodstock (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 908 days.

(21) Appl. No.: 17/279,351

(22) PCT Filed: Sep. 27, 2019

(86) PCT No.: PCT/EP2019/076187
§ 371 (c)(1),
(2) Date: Mar. 24, 2021

(87) PCT Pub. No.: WO2020/065010
PCT Pub. Date: Apr. 2, 2020

(65) Prior Publication Data
US 2021/0393882 A1    Dec. 23, 2021

(30) Foreign Application Priority Data
Sep. 28, 2018    (GB) ...................................... 1815824

(51) Int. Cl.
*A61M 5/315* (2006.01)
*A61M 5/31* (2006.01)
(52) U.S. Cl.
CPC ...... *A61M 5/31501* (2013.01); *A61M 5/3134* (2013.01); *A61M 5/3137* (2013.01); (Continued)
(58) Field of Classification Search
CPC ............ A61M 5/31501; A61M 5/3243; A61M 5/3271; A61M 2005/3265; (Continued)

(56) References Cited

U.S. PATENT DOCUMENTS

| 7,452,324 B2 | 11/2008 | Besing | |
| 2008/0027381 A1* | 1/2008 | Smith | ................. A61M 5/3234 |
| | | | 604/110 |

(Continued)

FOREIGN PATENT DOCUMENTS

| CA | 3026708 A1 | 11/2017 |
| GB | 2546499 A | 7/2017 |

(Continued)

OTHER PUBLICATIONS

International Search Report and Written Opinion of the International Searching Authority from corresponding PCT Application No. PCT/EP2019/076187, dated Jan. 28, 2020 (19 pages).

(Continued)

*Primary Examiner* — Emily L Schmidt
*Assistant Examiner* — Samuel J Marrison
(74) *Attorney, Agent, or Firm* — QUARLES & BRADY LLP

(57) ABSTRACT

A safety syringe comprising a barrel having an opening at an end thereof and a bung positioned in the barrel and creating a volume between the opening and the bung. The safety syringe also comprises a handle portion secured to the barrel and a syringe plunger slidably engaged with the handle portion and moveable within the barrel on an inward stroke to drive the bung forwards within the barrel to cause a substance within the volume to be expelled from the opening. The safety syringe further comprises a rotation mechanism configured to rotate the syringe plunger within the barrel at a point during the inward stroke when the syringe plunger is in contact with the bung, such that a rotational force is applied to the barrel and a brake connected to the handle portion and configured to provide a frictional force to resist the rotational force applied to the barrel.

18 Claims, 12 Drawing Sheets

(52) U.S. Cl.
  CPC . *A61M 5/31585* (2013.01); *A61M 2005/3131*
    (2013.01); *A61M 2005/3139* (2013.01); *A61M*
    *2005/3143* (2013.01)

(58) Field of Classification Search
  CPC .. A61M 2005/3139; A61M 2005/3143; A61M
    2005/3151; A61M 2005/3142; A61M
    2005/2407; A61M 2005/3131
  See application file for complete search history.

(56)                References Cited

U.S. PATENT DOCUMENTS

| | | | |
|---|---|---|---|
| 2013/0184655 A1 | 7/2013 | Lanzi et al. | |
| 2013/0245492 A1 | 9/2013 | Klenk et al. | |
| 2013/0245596 A1* | 9/2013 | Cabiri | A61M 5/14248 |
| | | | 604/152 |
| 2016/0121050 A1* | 5/2016 | Fabien | A61M 5/28 |
| | | | 604/228 |
| 2017/0080157 A1* | 3/2017 | Cabiri | A61M 5/31511 |
| 2017/0165423 A1 | 6/2017 | Holland | |

FOREIGN PATENT DOCUMENTS

| | | | |
|---|---|---|---|
| JP | 2017523821 A | 12/2018 | |
| WO | WO-02087670 A1 * | 11/2002 | A61M 5/3129 |
| WO | 2017125732 A1 | 7/2017 | |
| WO | 2017204787 A1 | 11/2017 | |

OTHER PUBLICATIONS

Search and Examination Report, related UK Application No. GB1815824.6, mailed Mar. 25, 2019, (9 pages).
International Preliminary Report on Patentability from corresponding PCT Application No. PCT/EP2019/076187 dated Apr. 8, 2021 (13 pages).
China National Intellectual Property Administration, First Office Action for corresponding Chinese Patent Application No. 201980071552.2, issued on Jun. 24, 2022 [12 pgs].

* cited by examiner

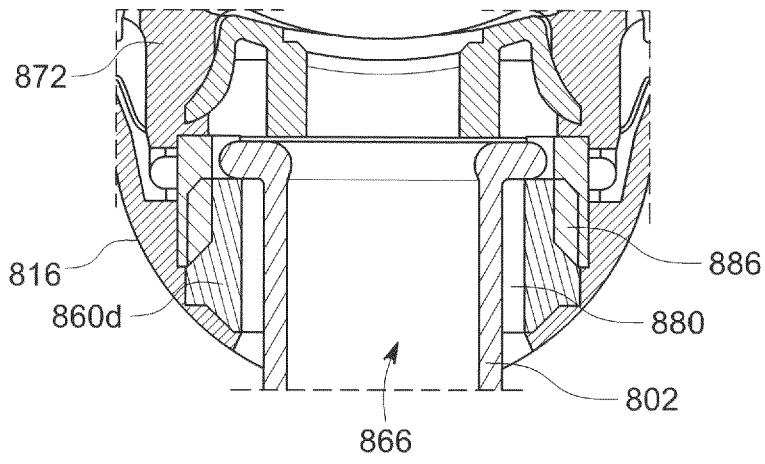
FIG. 8d
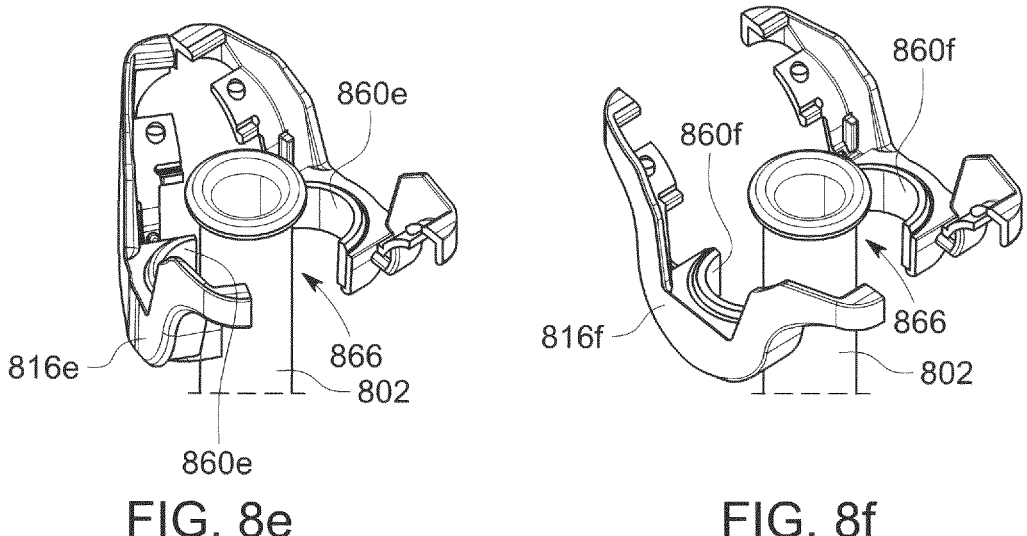
FIG. 8e                          FIG. 8f

SAFETY SYRINGE

CROSS-REFERENCE TO RELATED APPLICATIONS

The present application represents the United States National Stage of International Application No. PCT/EP2019/076187, filed Sep. 27, 2019, which relates to and claims priority to British Patent Application Serial No. GB 1815824.6, filed Sep. 28, 2018, both of which are incorporated herein by reference in their entirety.

TECHNICAL FIELD

The invention relates to safety syringes and apparatus for fitting to syringes to convert them to safety syringes. In particular embodiments, the invention relates to, but is not necessarily limited to, passive safety syringes and associated devices.

BACKGROUND

Broadly, syringes comprise a barrel having a hypodermic needle at one end and a plunger configured to move within the barrel such that an inward stroke of the plunger causes a substance contained within the barrel to be expelled from the needle.

Safety syringes typically include some form of safety mechanism to protect healthcare workers from the hypodermic needle after it has been injected into a patient. Exemplary safety syringes may include a sheath for covering the needle, or may cause the needle to retract within the barrel of the syringe.

Safety syringes may be broadly split into 'active' and 'passive'. Active safety syringes typically require some action by a user of the syringe to engage the safety mechanism. Such action may be taken after removal of the needle from the patient, or may be taken during removal of the needle from the patient. Typically, the action required to engage the safety mechanism is separate from the action required to cause the inward stroke of the plunger. Passive safety syringes typically engage the safety mechanism without any specific action by the user, that is, without any action other than that usually taken to use the syringe.

Safety mechanisms for covering the needle after use of the syringe should be sufficient to prevent stick injuries to the user, including stick injuries if the user accidentally contacts the safety mechanism itself.

SUMMARY

According to the invention in a first aspect, there is provided a safety syringe comprising: a barrel having an opening at an end thereof; a bung positioned in the barrel and creating a volume between the opening and the bung; a handle portion secured to the barrel; a syringe plunger slidably engaged with the handle portion and moveable within the barrel on an inward stroke to drive the bung forwards within the barrel to cause a substance within the volume to be expelled from the opening; a rotation mechanism configured to rotate the syringe plunger within the barrel at a point during the inward stroke when the syringe plunger is in contact with the bung, such that a rotational force is applied to the barrel; and a brake connected to the handle portion and configured to provide a frictional force to resist the rotational force applied to the barrel. The syringe rotation mechanism may rotate the syringe plunger under a force applied by the user to drive the syringe plunger into the barrel.

Optionally, the handle portion is configured to hold the brake in compression, directly or indirectly, against the barrel.

Optionally, the brake is configured to apply the frictional force to a sidewall of the barrel.

Optionally, the brake forms at least part of an aperture in the handle portion in which the barrel is received.

Optionally, the brake forms at least part of an inner circumference of the aperture.

Optionally, the barrel is received within the aperture such that an interference fit is formed between the barrel and the brake.

Optionally, the brake comprises a grommet. The grommet may be resiliently deformable and in some examples may be elastomeric.

Optionally, before the barrel is received within the aperture, a diameter of the aperture is greater than a diameter of the barrel of the syringe, and wherein the brake is engageable upon receipt of the barrel within the aperture.

Optionally, the grommet is configured to interact with the barrel and/or the handle portion to engage the brake by compression of the grommet by a flange of the barrel and/or lateral movement of the grommet to meet a sidewall of the barrel.

Optionally, the handle portion comprises a reaction surface configured to compress and/or laterally move the grommet on application of an axial force on the grommet with respect to the handle portion.

Optionally, the reaction surface is angled to displace the grommet laterally inwards on axial movement of the grommet with respect to the handle portion.

Optionally, the reaction surface is configured to resist axial movement of the grommet with respect to the handle portion, such that the axial force on the grommet compresses and/or laterally expands the grommet.

Optionally, a rearward surface of the grommet is configured to contact the flange of the barrel when the barrel is received in the aperture.

Optionally, the rearward surface extends from a rearward end of the aperture.

Optionally, the handle portion comprises a bottom out face configured to contact a flange of the barrel upon receipt of the barrel within the aperture for preventing forward movement of the barrel.

Optionally, the handle portion is operable to open the aperture, and is further operable to close the aperture after insertion of the barrel within the aperture to engage the brake.

Optionally, the handle portion comprises two portions, separable to open the aperture.

Optionally, the two portions are connected by a hinge.

Optionally, safety syringe further comprises an insert fittable to the handle portion and configured to engage the brake.

Optionally, the insert comprises one or more lateral displacement features configured to interact with the grommet to displace the grommet laterally inwards.

Optionally, the brake is in contact with a top or rearward surface of the barrel.

Optionally, the insert is configured to hold the brake in compression against the top or rearward surface of the barrel.

Optionally the safety syringe further comprises a safety plunger longitudinally coupled to the syringe plunger such that an inward stroke of the safety plunger causes the inward stroke of the syringe plunger.

Optionally, the safety syringe further comprises a sheath directly or indirectly slidably engaged with the handle portion and configured to cover at least partially the opening in the barrel.

Optionally, the safety plunger is configured to longitudinally couple to the sheath at a first point on the inward stroke and is configured to longitudinally decouple from the syringe plunger at a second point on the inward stroke such that the safety plunger is longitudinally moveable independently of the syringe plunger, and wherein further movement of the safety plunger after longitudinally decoupling causes the sheath to at least partially cover the opening in the barrel.

Optionally, prior to operation of the safety syringe, the safety plunger is longitudinally decoupled from the sheath and configured to longitudinally couple to the sheath at the first point on the inward stroke.

Optionally, the rotational force is applied to the barrel after longitudinal decoupling of the safety plunger and the syringe plunger.

Optionally, the rotation mechanism comprises a first screw thread on the safety plunger and a second screw thread on the syringe plunger and configured to engaged with the first screw thread to rotate the syringe plunger on movement of the safety plunger after longitudinal decoupling.

Optionally, the rotation mechanism is further configured to control a rate of travel of the safety plunger after longitudinal decoupling.

According to the invention in a further aspect there is provided a safety syringe apparatus for use with a syringe comprising a barrel having an opening at an end thereof and a bung positioned in the barrel and creating a volume between the opening and the bung, the syringe apparatus comprising: a handle portion for securing to the barrel; a syringe plunger slidably engaged with the handle portion and configured, when the handle portion is secured to the barrel, to be moveable within the barrel on an inward stroke to drive the bung forwards within the barrel to cause a substance within the volume to be expelled from the opening; a rotation mechanism configured to rotate the syringe plunger within the barrel at a point during the inward stroke when the syringe plunger is in contact with the bung, such that a rotational force is applied to the barrel; and a brake connected to the handle portion and configured to provide a frictional force to resist the rotational force applied to the barrel.

According to the invention in a further aspect, there is provided a kit of parts for forming an apparatus for use with a syringe comprising a barrel having an opening at an end thereof and a bung positioned in the barrel and creating a volume between the opening and the bung, the kit of parts comprising: a handle portion for securing to the barrel; a syringe plunger for slidable engagement with the handle portion and configured, when the handle portion is secured to the barrel, to be moveable within the barrel on an inward stroke to drive the bung forwards within the barrel to cause a substance within the volume to be expelled from the opening; a rotation mechanism configured to rotate the syringe plunger within the barrel at a point during the inward stroke when the syringe plunger is in contact with the bung, such that a rotational force is applied to the barrel; and a brake connectable to the handle portion and configured to provide a frictional force to resist the rotational force applied to the barrel.

Optionally, the handle portion is configured, when secured to the barrel, to hold the brake in compression, directly or indirectly, against the barrel.

Optionally, the kit of parts further comprises: a safety plunger configured to be longitudinally coupled to the syringe plunger such that an inward stroke of the safety plunger causes the inward stroke of the syringe plunger; and a sheath configured to cover at least partially the opening in the barrel, wherein the safety plunger is configured to longitudinally couple to the sheath at a first point on the inward stroke and is configured to longitudinally decouple from the syringe plunger at a second point on the inward stroke such that the safety plunger is longitudinally moveable independently of the syringe plunger, and wherein further movement of the safety plunger after longitudinal decoupling causes the sheath to at least partially cover the opening in the barrel.

According to the invention in a further aspect, there is provided a safety syringe comprising: a barrel having an opening at an end thereof and having a hypodermic needle fitted thereto; a bung positioned in the barrel and creating a volume between the opening and the bung; a handle portion secured to the barrel; a syringe plunger slidably engaged with the handle portion and configured to be moveable within the barrel on an inward stroke to drive the bung forwards within the barrel to cause a substance within the volume to be expelled from the opening; a sheath directly or indirectly slidably engaged with the handle portion and deployable at a point on the inward stroke before an end of the inward stroke and under control of a force applied to the syringe plunger, to at least partially cover the hypodermic needle, wherein, in use, deployment of the sheath causes the sheath to contact a surface of an injection site to withdraw the hypodermic needle from the injection site.

Optionally, at least a portion of the substance remains in the barrel at the point on the inward stroke before the end of the inward stroke.

Optionally, the at least a portion of the substance has a volume in a range from 0.01 ml to 0.2 ml; 0.01 ml to 0.05 ml; or 0.01 ml to 0.02 ml.

Optionally, the sheath is configured to move beyond a forward end of a neck of the barrel of the syringe at the point on the inward stroke before the end of the inward stroke.

Optionally, the at least a portion of the substance remains in the barrel when the sheath has moved beyond the forward end of the neck of the barrel.

Optionally, the safety syringe further comprises a safety plunger longitudinally coupled to the syringe plunger such that an inward stroke of the safety plunger causes the inward stroke of the syringe plunger.

Optionally, the safety plunger is configured to longitudinally couple to the sheath at the point on the inward stroke of the syringe plunger such that further movement on the inward stroke of the safety plunger deploys the sheath.

Optionally, the sheath comprises at least one longitudinal channel.

Optionally, the safety plunger comprises at least one arm received within the at least one channel, and arranged to allow travel of the at least one arm within the at least one channel.

Optionally, the at least one arm is configured to contact a forward end of the at least one channel at the point on the inward stroke of the syringe plunger.

Optionally, the at least one arm is configured to contact the forward end of the at least one channel to longitudinally couple the safety plunger to the sheath.

According to the invention in a further aspect, there is provided a safety syringe apparatus for use with a syringe comprising a barrel having an opening at an end thereof and having a hypodermic needle fitted thereto and a bung positioned in the barrel and creating a volume between the opening and the bung, the safety syringe apparatus comprising: a handle portion for securing to the barrel; a syringe plunger, slidably engaged with the handle portion and configured, when the handle portion is secured to the barrel, to be moveable within the barrel on an inward stroke to drive the bung forwards to cause a substance within the volume to be expelled from the opening; and a sheath directly or indirectly slidably engaged with the handle portion and deployable at a point on the inward stroke before an end of the inward stroke and under control of a force applied to the syringe plunger, to at least partially cover the hypodermic needle, wherein, in use, deployment of the sheath causes the sheath to contact a surface of an injection site to withdraw the hypodermic needle from the injection site.

According to the invention in a further aspect, there is provided a kit of parts for forming an apparatus for use with a syringe comprising a barrel having an opening at an end thereof and having a hypodermic needle fitted thereto and a bung positioned in the barrel and configured to create a volume between the opening and the bung, the kit of parts comprising: a handle portion for securing to the barrel; a syringe plunger for slidable engagement with the handle portion and configured, when the handle portion is secured to the barrel, to be moveable within the barrel on an inward stroke to drive the bung forwards within the barrel to cause a substance within the volume to be expelled from the opening; and a sheath for direct or indirect slidable engagement with the handle portion and configured, when engaged with the handle portion, to be deployable at a point on the inward stroke before an end of the inward stroke and under control of a force applied to the syringe plunger, to at least partially cover the hypodermic needle, wherein, in use, deployment of the sheath causes the sheath to contact a surface of an injection site to withdraw the hypodermic needle from the injection site.

According to the invention in a further aspect, there is provided a safety syringe comprising: a barrel having an opening at an end thereof; a bung positioned in the barrel and creating a volume between the opening and the bung; a handle portion secured to the barrel; a syringe plunger slidably engaged with the handle portion and moveable within the barrel on an inward stroke to drive the bung forwards within the barrel to cause a substance within the volume to be expelled from the opening; and a sheath directly or indirectly slidably engaged with the handle portion and deployable to cover at least partially the opening in the barrel after use of the syringe, wherein the sheath at least partially surrounds an outer wall of the barrel defining an inner dimension of the sheath, and wherein the sheath comprises an aperture at a forward end, the aperture having a dimension less than an outer dimension of the barrel.

Optionally, a lip is formed between an outer edge of the aperture and an inner wall of the sheath.

Optionally, the lip is positioned in contact with a shoulder of the barrel.

Optionally, the barrel of the syringe has a diameter greater than 8.15 mm and/or has a diameter of 12 mm.

Optionally, the sheath is deployable to an extent at which a forward end of the sheath is in a range from 2 mm to 10 mm beyond a forward end of a hypodermic needle fitted to the opening of the barrel.

According to the invention in a further aspect, there is provided a safety syringe apparatus for use with a syringe, the syringe comprising a barrel having an opening at an end thereof and a bung positioned in the barrel and creating a volume between the opening and the bung, the safety syringe apparatus comprising: a handle portion for securing to the barrel; a syringe plunger slidably engaged with the handle portion and configured, when the handle portion is secured to the barrel, to be moveable within the barrel on an inward stroke to drive the bung forwards within the barrel to cause a substance within the volume to be expelled from the opening; a sheath directly or indirectly slidably engaged with the handle portion and deployable to cover at least partially the opening in the barrel after use of the syringe, wherein, when the safety syringe apparatus is fitted to a syringe, the sheath at least partially surrounds an outer wall of the barrel defining an inner dimension of the sheath, and wherein the sheath comprises an aperture at a forward end, the aperture having a dimension less than the inner dimension of the sheath.

According to the invention in a further aspect there is provided a kit of parts for forming an apparatus for use with a syringe comprising a barrel having an opening at an end thereof and a bung positioned in the barrel and creating a volume between the opening and the bung, the kit of parts comprising: a handle portion for securing to the barrel; a syringe plunger for slidable engagement with the handle portion and configured, when the handle portion is secured to the barrel, to be moveable within the barrel on an inward stroke to drive the bung forwards within the barrel to cause a substance within the volume to be expelled from the opening; and a sheath for direct or indirect slidable engagement with the handle portion and configured to be deployable to cover at least partially the opening in the barrel after use of the syringe, wherein, when the kit of parts is assembled on a syringe, the sheath at least partially surrounds an outer wall of the barrel defining an inner dimension of the sheath, and wherein the sheath comprises an aperture at a forward end, the aperture having a dimension less than the inner dimension of the sheath.

BRIEF DESCRIPTION OF THE DRAWINGS

FIGS. 8a to 8f show exemplary brake configurations.

DETAILED DESCRIPTION

Figure 1:
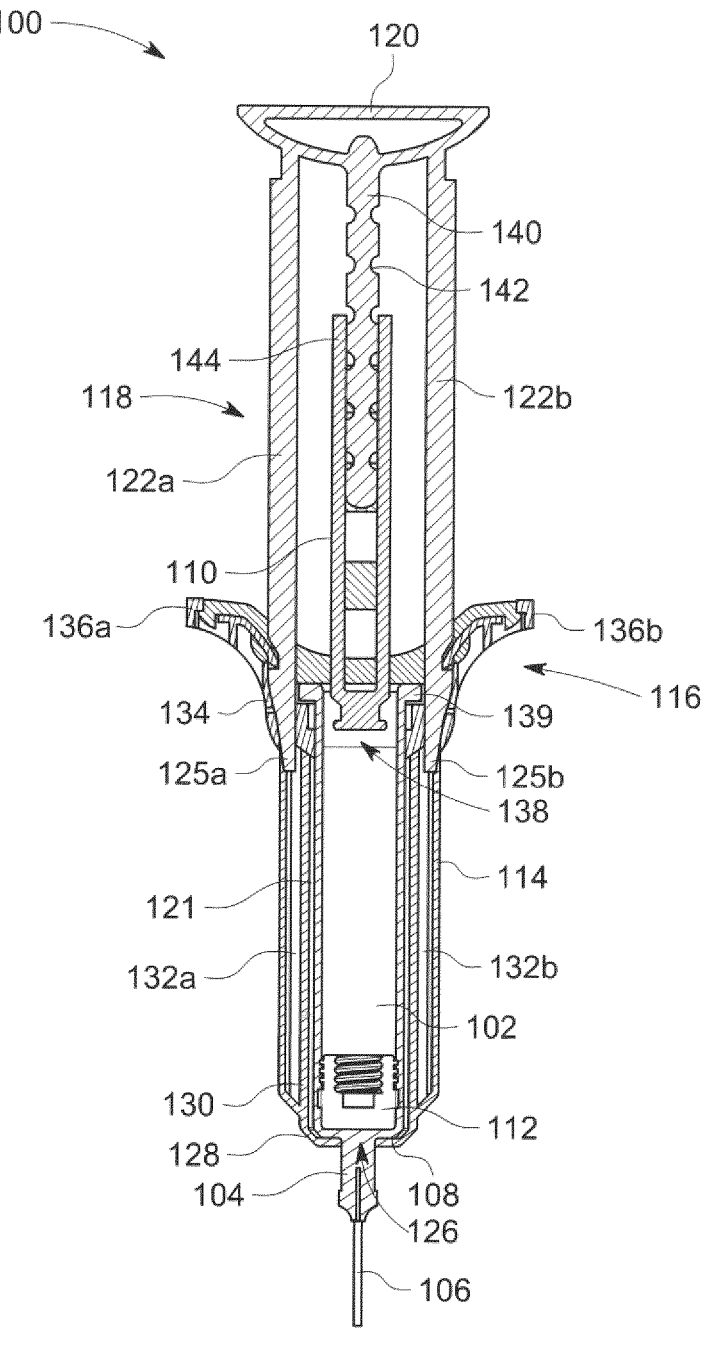
FIG. 1 is a section view of a safety syringe.

Generally disclosed herein are safety syringes comprising a sheath which is moveable from a first position in which the needle is exposed, to a deployed position in which the needle of the syringe is covered. The sheath may be moveable under a force applied by a user during normal operation of the syringe, that is, during an inward stroke of a syringe plunger to expel a substance from a barrel of the syringe. In exemplary safety syringes, the sheath may travel along the barrel of the syringe during the inward stroke and then move beyond an end of the barrel to cover the needle. Exemplary sheaths therefore comprise an aperture at forward and rearward ends allowing the sheath to move along the length of the barrel.

In order to prevent stick injuries, the forward end of the sheath (and therefore the aperture at the forward end) may be required to extend a certain distance past the end of the needle when the sheath has been fully deployed. This reduces the risk that a finger or other part of a user's body will enter the aperture and contact the needle. One test to determine the distance that the forward end of the sheath may extend past the end of needle involves a 12 mm sphere being held against the aperture at the forward end of the sheath once the sheath has been deployed. The dimensions of the sheath should be such that the 12 mm sphere does not touch the needle when held against the aperture.

The inventors have realised that when using larger diameter syringe barrels, the distance that the sheath has to extend past the needle in order to meet the requirements of the test is increased. In exemplary safety syringes, this may increase the overall stroke length of a plunger of the syringe, which in turn can impact on the ability of the user to stretch their hand to operate the syringe. The inventors have further realised that reducing the diameter of the aperture at the forward end of the sheath will reduce the distance the sheath is required to travel beyond the end of the needle.

Exemplary sheaths may therefore be configured to at least partially surround the barrel, defining an inner dimension of the sheath. The aperture at the forward end of the sheath has a dimension less than the inner dimension of the sheath. The aperture of the sheath may have a dimension less than an outer dimension of the barrel. In some arrangements, the aperture at the forward end of the sheath may be positioned forward of a main portion of the barrel before deployment of the sheath, and may be located adjacent a neck of the barrel.

Throughout the specification, the term "forward" refers to the patient facing end of the safety syringe. In other words, the forward end of the safety syringe is the end proximal to the injection site during use. Similarly, the terms "rear" or "rearward" refer to the non-patient end of the safety syringe or component thereof. In other words, the term "rearward" means distant or remote from the injection site during use. Other relative terms such as axial, longitudinal and the like are used to aid description of the device.

FIG. 1 shows a safety syringe 100 comprising a syringe comprising a barrel 102, a barrel neck 104 and a hypodermic needle 106. The hypodermic needle 106 is hollow. The barrel 102 is configured to receive a substance to be injected into a patient. The barrel comprises a shoulder 108, which narrows towards the barrel neck 104. The barrel neck 104 comprises an opening configured to receive the hypodermic needle 106 such that a fluid path exists between the barrel 102 and the hollow channel of the needle 106. In exemplary safety syringes 100, the needle 106 is fixedly attached to the barrel 102 via the barrel neck 104. In other exemplary safety syringes 100, the needle 106 may be removably attached to the barrel 102. In such safety syringes 100, the needle 106 may be replaced by other needles of the same or a different type.

The syringe further comprises a syringe plunger 110 and a bung 112. The syringe plunger 110 is received inside the barrel 102 and is configured to connect to the bung 112. The syringe plunger 110 and the bung 112 are configured to move within the barrel 102. The syringe plunger 110 may move on an inward stroke, wherein the syringe plunger 110 moves further into the barrel 102, or an outward stroke wherein the syringe plunger 110 is drawn out of the barrel. The syringe plunger 110 and the bung 112 are configured such that the inward stroke of the syringe plunger 110 causes inward movement of the bung 112 and a substance held in the barrel (in a volume formed between the bung 112 and the end of the barrel neck 104) to be expelled from the open end of the barrel 102 by the bung 112 and through the hypodermic needle 106.

The safety syringe 100 further comprises a safety syringe apparatus comprising a sheath 114, a handle portion 116 fixed in relation to the barrel 102, and a safety plunger 118.

In the exemplary apparatus of FIG. 1, the safety plunger 118 comprises a head 120 and arms 122a, 122b. The arms 122a, 122b may comprise sheath contact surfaces configured to engage with the sheath 114 at a point on an inward stroke of the safety plunger 118. The sheath contact surfaces may engage with the sheath 114 by directly contacting a surface of the sheath 114. In the exemplary apparatus of FIG. 2a, the sheath contact surfaces 123a, 123b are located at a rearward position on the arms 122a, 122b and are configured to contact a surface of the sheath 119a, 119b located at a rearward position on the sheath 118 (as shown in FIG. 2b). In alternative arrangements (such as that shown in FIG. 3) the sheath contact surfaces 123a, 123b may be located at a forward end of the arms 122a, 122b and configured to contact a surface of the sheath located at a forward position on the sheath. For example, the sheath contact surfaces may be the end faces of the arms 125a, 125b.

The sheath 114 surrounds an outer wall 121 of the barrel 102, which defines an inner dimension of the sheath 114. The sheath 114 comprises an aperture 126 at a forward end. The aperture 126 may be positioned forward of the shoulder 108 before deployment of the sheath 114. The aperture 126 is of smaller dimension (e.g. diameter) than an inner dimension (e.g. diameter) of the sheath 114. In exemplary safety syringes, the aperture 126 of the sheath 110 may be of a smaller dimension (e.g. diameter) than the outer wall 121 of the barrel 102.

In the exemplary safety syringe of FIG. 1, the sheath comprises a lip 128. The lip 128 extends radially inwards from an inner wall 130 of the sheath 114 to define the aperture 126. In FIG. 1, the lip extends inwards to a point such that the diameter of the aperture is of smaller diameter than the outer wall 121 of the barrel. The lip 128 may be configured to contact the shoulder 108 of the safety syringe 100 before deployment of the sheath. In the arrangement of FIG. 1, the lip 128 is configured to contact a forward surface of the shoulder 108 of the safety syringe 100 before movement of the sheath to cover the needle 106. In other arrangements, the lip 128 may be at any point forward of the shoulder 108 before deployment of the sheath 114, thereby allowing the aperture 126 to be of a smaller diameter than the outer diameter of the barrel 102.

The sheath 114 comprises channels 132a, 132b. The channels 132a, 132b correspond to the arms 122a, 122b of the safety plunger 118 and are configured to allow travel of one of the arms 122a, 122b, within each channel 132a, 132b during an inward stroke.

The sheath 114 of FIG. 1 is shown to surround the barrel 102 along substantially the entire length of the barrel 102. In alternative arrangements, the sheath may surround the barrel only at a forward, needle end of the barrel 102. In such arrangements, the sheath 114 may be of a length such that when the sheath covers the needle 106, at least a portion of the sheath still surrounds the barrel 102.

The handle portion 116 comprises a main body 134 and flanges 136a, 136b extending laterally from the main body 134. The main body 134 comprises a portion that surrounds the barrel 102 and is fixed thereto. The flanges 136a, 136b are configured to receive the index finger and middle finger of a user while the thumb applies a force to the head 120 of the safety plunger 118, although any combination of fingers and/or thumb could be used. The handle portion 116 is fixed to the barrel 102 by an aperture 138 configured to receive an end of the barrel 102 at a distal end to the opening coupled to the needle 106. In the embodiment of FIG. 1, the barrel 102 comprises a radially protruding lip 139 that is received by the handle portion 116, however in alternative arrangements, the handle portion 116 may receive syringe barrels without radially protruding lips.

The sheath 114 may be at least partially received within the main body 134 of the handle portion 116.

The arms 122a, 122b of the safety plunger 118 are configured to pass through the handle portion 116 such that the safety plunger 118 may move in its stroke relative to the handle portion 116 and, therefore, the barrel 102.

The safety syringe 100 may comprise a coupling arrangement configured to couple the safety plunger 118 and the syringe plunger 110 such that movement of the safety plunger 118 on an inward stroke causes an inward stroke of the syringe plunger 110. The safety syringe 100 may comprise a decoupling arrangement configured to decouple the safety plunger 118 and the syringe plunger 110, such that relative movement of the safety plunger 118 with respect to the syringe plunger 110 is possible.

The skilled person will appreciate that many coupling and decoupling mechanisms may be utilised. For example one of the syringe plunger and the safety plunger may comprise coupling recesses configured to receive coupling lugs on the other of the syringe plunger and the safety plunger. The lugs may be configured to engage with the coupling recesses to couple the safety plunger and the syringe plunger and disengage from the coupling recesses to decouple the safety plunger and the syringe plunger. Alternative coupling and decoupling arrangements are described below.

Figure 2A:
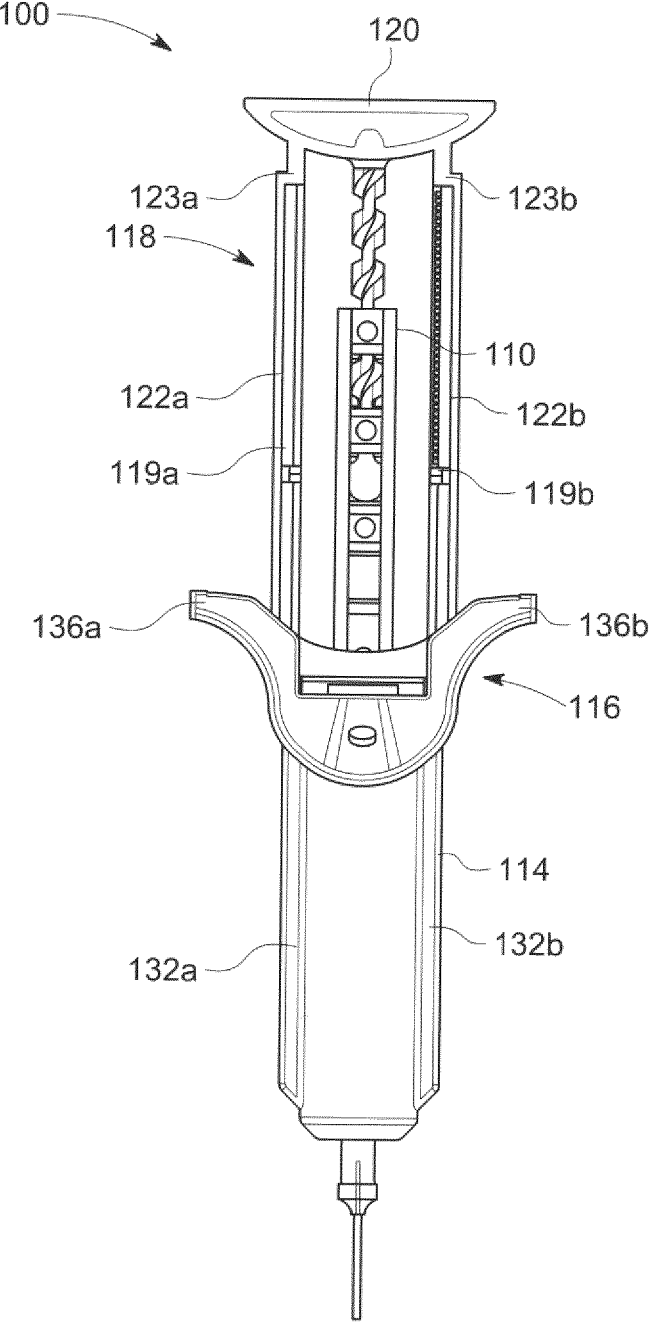
FIG. 2a is a plan view of a safety syringe at a first point along its inward stroke.
Figure 2B:
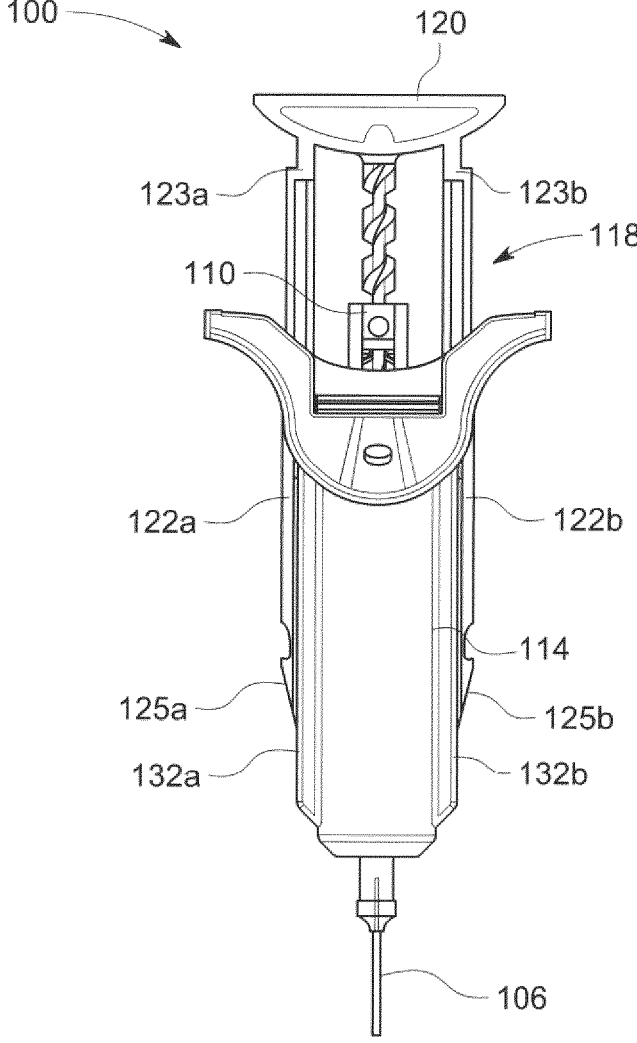
FIG. 2b is a plan view of a safety syringe at a second point along its inward stroke.
Figure 2C:
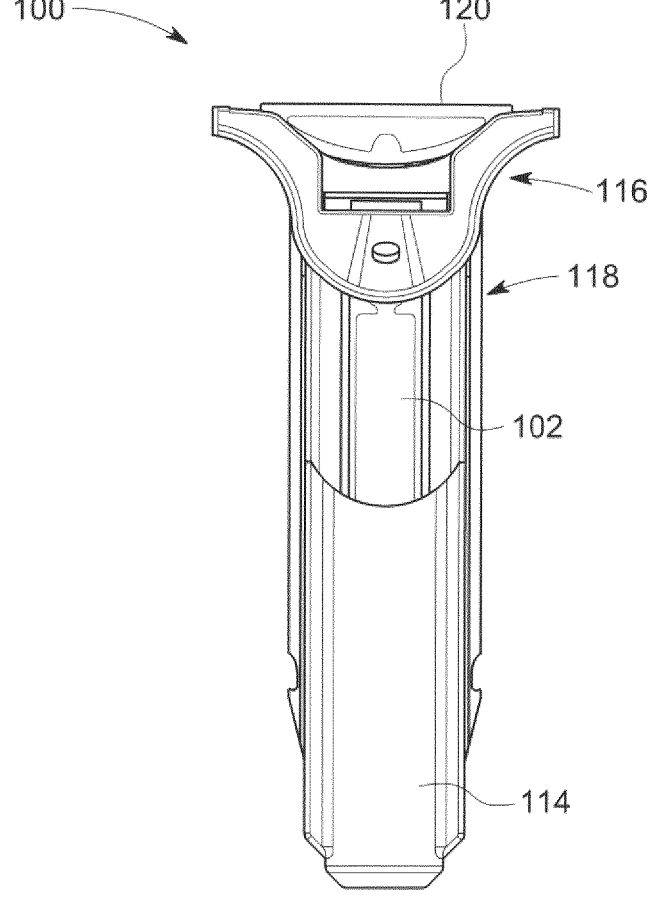
FIG. 2c is a plan view of a safety syringe at a third point along its inward stroke.

FIGS. 2a-c show views of the safety syringe 100 at various positions along the inward stroke of the safety plunger 118. The operation of the safety syringe 100 will be described below with reference to FIGS. 2a-c.

FIG. 2a shows the safety syringe 100 with both syringe plunger 110 and the safety plunger 118 fully extended and at the outermost points of their strokes. The syringe plunger 110 is coupled to the safety plunger 118.

A user may place an index finger and middle finger of one hand against the flanges 136a, 136b of the handle portion 116 and the thumb of the same hand on the head 120 of the safety plunger 118. The user then applies a relative force to the head 120 and the handle portion 116 by closing the thumb towards the index and middle fingers. For the sake of clarity, this relative force will be considered herein as a force on the head 120.

The force applied to the head 120 begins the inward stroke of the safety plunger 118. As the safety plunger 118 and the syringe plunger 110 are coupled, the inward stroke of the syringe plunger 110 also begins. That is, the syringe plunger 110 and the safety plunger 118 are longitudinally coupled in that they move together on an inward and/or outward stroke of the safety plunger 118. The arms 122a, 122b pass through the handle portion 116 and travel within the channels 132a, 132b of the sheath 114. The arms 122a, 122b of the safety plunger 118 continue to travel within the channels 132a, 132b until the sheath contact surfaces 123a, 123b engage with the sheath 114.

FIG. 2b shows the point at which the sheath contact surfaces 123a, 123b engage with the sheath 114 to provide longitudinal coupling of the safety plunger 118 and the sheath 114. In the exemplary arrangement shown in FIG. 2b, the sheath contact surfaces 123a, 123b of the safety plunger 118 engage faces of the sheath 119a, 119b located at a rearward end of the sheath channels 132a, 132b. In FIG. 2b, the engagement between the sheath contact surfaces 123a, 123b and the faces 119a, 119b of the sheath channels 132a, 132b is provided by abutment. The safety plunger 118 therefore couples to the sheath 114 such that continued application of the force on the head 120 of the safety plunger 118 on the inward stroke causes movement of the sheath to partially cover the needle 106.

Figure 3:
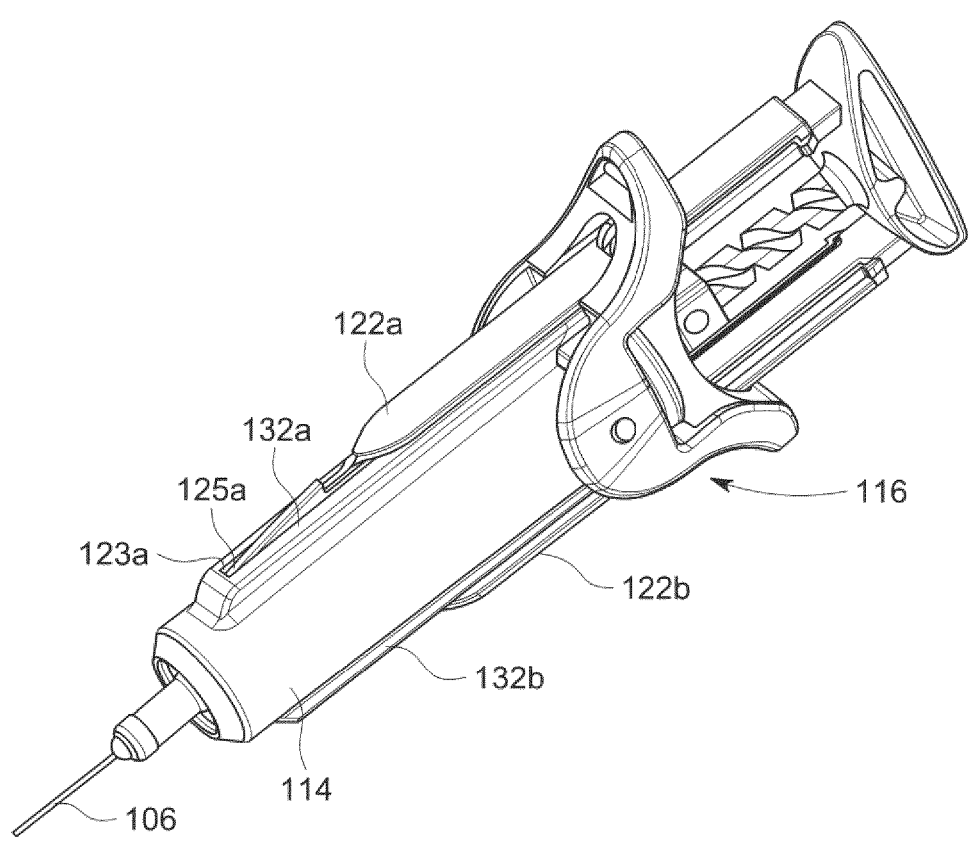
FIG. 3 is an isometric view of a safety syringe.

In alternative arrangements the end faces 125a, 125b of the arms 122a, 122b may contact a surface located at the forward end of the channels 132a, 132b to provide the abutment (see FIG. 3). Such an arrangement may be advantageous if the arms 122a, 122b are manufactured from a stronger material than the sheath 114, since any forward force applied to the sheath 114 would pass through the arms 122a, 122b as opposed to the comparatively weaker channels 132a, 132b of the sheath 114.

The point at which the longitudinal coupling between the safety plunger 118 and the sheath 114 occurs may be the point at which the syringe plunger 110 has completed its inward stroke. That is, the coupling may occur at the innermost point of the stroke of the syringe plunger 110, although this is not essential. Such arrangements ensure that all of the substance contained within the barrel 102 has been expelled from the syringe 100 before the sheath is deployed to cover the needle. In alternative arrangements the safety plunger 118 and the sheath 114 may longitudinally couple at a point before completion of the inward stroke of the syringe plunger 110 (this is described in further detail below).

In the exemplary arrangement of FIGS. 2a-c, the point at which the safety plunger 118 and the sheath 114 longitudinally couple is the point at which the syringe plunger 110 and the safety plunger 118 longitudinally decouple. Alternatively, the safety plunger 118 and the syringe plunger 110 may longitudinally decouple at a point before or after the longitudinal coupling of the safety plunger 118 and the sheath 114.

The safety plunger 118 is free to move longitudinally on an inward stroke relative to the syringe plunger 110 after longitudinal decoupling. For example, the safety plunger 118 may be free to move longitudinally, while the syringe plunger 110 remains substantially stationary longitudinally (this is described in further detail below). Alternatively, the rate of longitudinal movement of the safety plunger 118 may be different to the rate of longitudinal movement of the syringe plunger 110 after longitudinal decoupling. Continued application of force to the head 120 after longitudinal decoupling will continue the inward stroke of the safety plunger 118. Since the sheath 114 is longitudinally coupled to the safety plunger 118 by the sheath coupling surfaces 123*a*, 123*b*, continued inward movement of the safety plunger 118 results in inward movement of the sheath 114.

As a user continues to apply a force to the head 120, the safety plunger 118 continues to pass through the handle portion 116 and the sheath begins to move to at least partially surround the barrel neck 104.

As shown in FIG. 2*c*, when the inward stroke of the safety plunger 118 has been completed, the head 120 abuts the handle portion 116 and also abuts the head of the syringe plunger 110. In this position the sheath 114 has extended such that it surrounds the barrel neck 104 and the needle 106. The forward end of the sheath 114 extends beyond the tip of the needle 106 such that the needle is not exposed. In this position, the safety plunger 118 may lock in relation to the barrel 102 and needle 106, such that the needle 106 cannot become exposed. In exemplary safety syringes, the safety plunger 110 may become locked to the handle portion 116.

By positioning the aperture of the sheath 114 forward of the shoulder 108 of the barrel 102 before deployment of the sheath 114, the aperture 126 of the sheath may be reduced. This is because the aperture no longer has to extend around the diameter of the barrel 102 but only the barrel neck 104, which is of reduced dimension in comparison to the barrel 102. This means that the sheath 114 is not required to extend as far in front of the forward end of the needle 106 (compared with an aperture 126 equal to the diameter of the barrel) in order to prevent stick injuries. There is therefore no need to increase the distance by which the forward end of the sheath 118 extends past the forward end of the needle when the safety syringe apparatus is used with larger syringes (which typically have greater barrel diameters). For example, the barrel of the syringe may be greater than 8.05 mm (the typical diameter of a 1 ml syringe) and may be 10.75 mm (the typical diameter of a 2.25 ml syringe) or more. The aperture in the forward end of the sheath may have a diameter up to 2 mm less, up to 1 mm less, or in a range from 0.5 mm to 2 mm less than the diameter of the barrel Further, because the sheath is only required to travel a distance slightly over the length of the barrel neck 104 and the needle 106, the length of the inward stroke is not increased.

Figure 4:
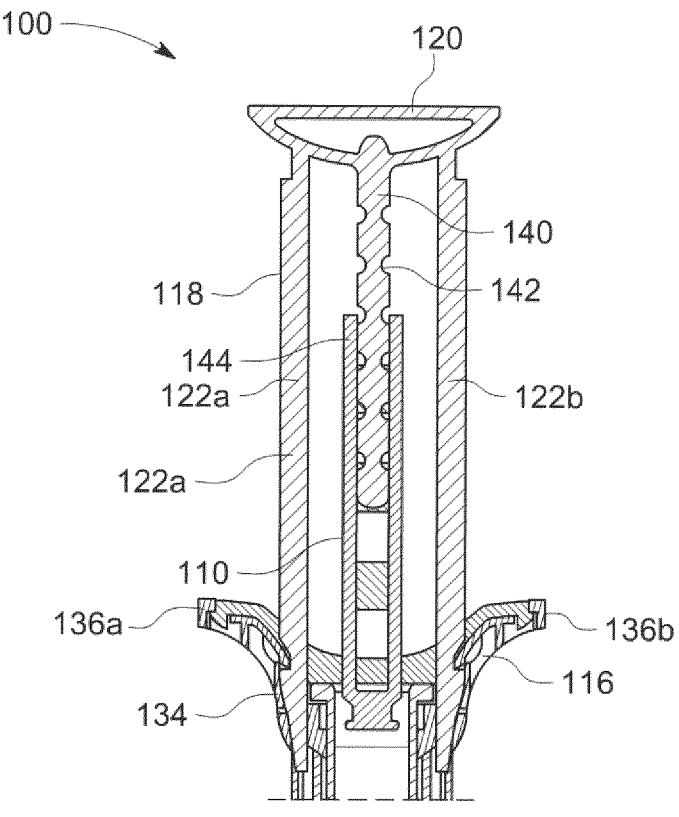
FIG. 4 is a schematic view of a rotation mechanism or a safety syringe.

Referring to FIG. 4, the safety syringe 100 may further comprise an apparatus to control a rate of deployment of the sheath after longitudinal decoupling of the safety plunger 118 and the syringe plunger. This apparatus may be considered a rotation mechanism in that it imparts a rotational force on the barrel, as explained below. The rotational force is a by-product of the rate control provided by the mechanism itself. The skilled person will appreciate that other mechanisms may impart a rotational force on a barrel of a syringe and the methods and apparatus disclosed herein are equally applicable to those mechanisms as to the specific mechanism described below. Exemplary methods and apparatus may be used in any arrangement where rotation of the barrel is to be resisted.

An exemplary apparatus comprises a first screw thread 142 on the safety plunger 118 and a corresponding second screw thread 144 on the syringe plunger 110 and configured to engage the first screw thread 142.

The safety syringe is therefore configured to limit and/or control the rate of deployment of the sheath and thereby a rate of extraction of a needle 106 from a subject. The exemplary apparatus shown comprises a member 140 that is configured to extend into the syringe plunger 110, which comprises the second thread internally, after longitudinal decoupling.

After decoupling, the first screw thread 142 on the member 140 of the safety plunger 118 interacts with the second screw thread 144 in the syringe plunger 110 to impart a rotational force. The rotational force causes the syringe plunger to rotate within a barrel 102 of the safety syringe 100. Therefore, even though they are longitudinally decoupled, the safety plunger 118 and the syringe plunger 110 remain rotationally coupled.

The rotation of the syringe plunger 110 within the barrel 102 is resisted by a friction between a forward end of the syringe plunger 110 and the bung 112 and this limits and/or controls the rate of movement of the safety plunger 118 after decoupling from the syringe plunger 110.

The bung 112 may be formed of a resiliently deformable material, such as a rubberised material, and has a diameter slightly larger than an internal diameter of the barrel 102, such that a seal is formed when the bung 112 is inserted within the barrel 102. That seal may also provide resistance to the rotational motion of the syringe plunger 110 within the barrel 102. Alternatively or in addition, the screw threads 142, 144 may be configured to resist rotational motion of the syringe plunger 110 for example by friction between the screw threads 142, 144 themselves. The interacting surfaces of the screw threads 142, 144 may be configured to provide a particular friction force. Further, the syringe plunger 110 may not be fixed to the bung 112 and may be free to rotate therein. In such arrangements, at least part of the force resisting rotation of the syringe plunger 110 may be provided by friction between the syringe plunger 110 and the bung 112.

Figures 5A, 5B, 5C:
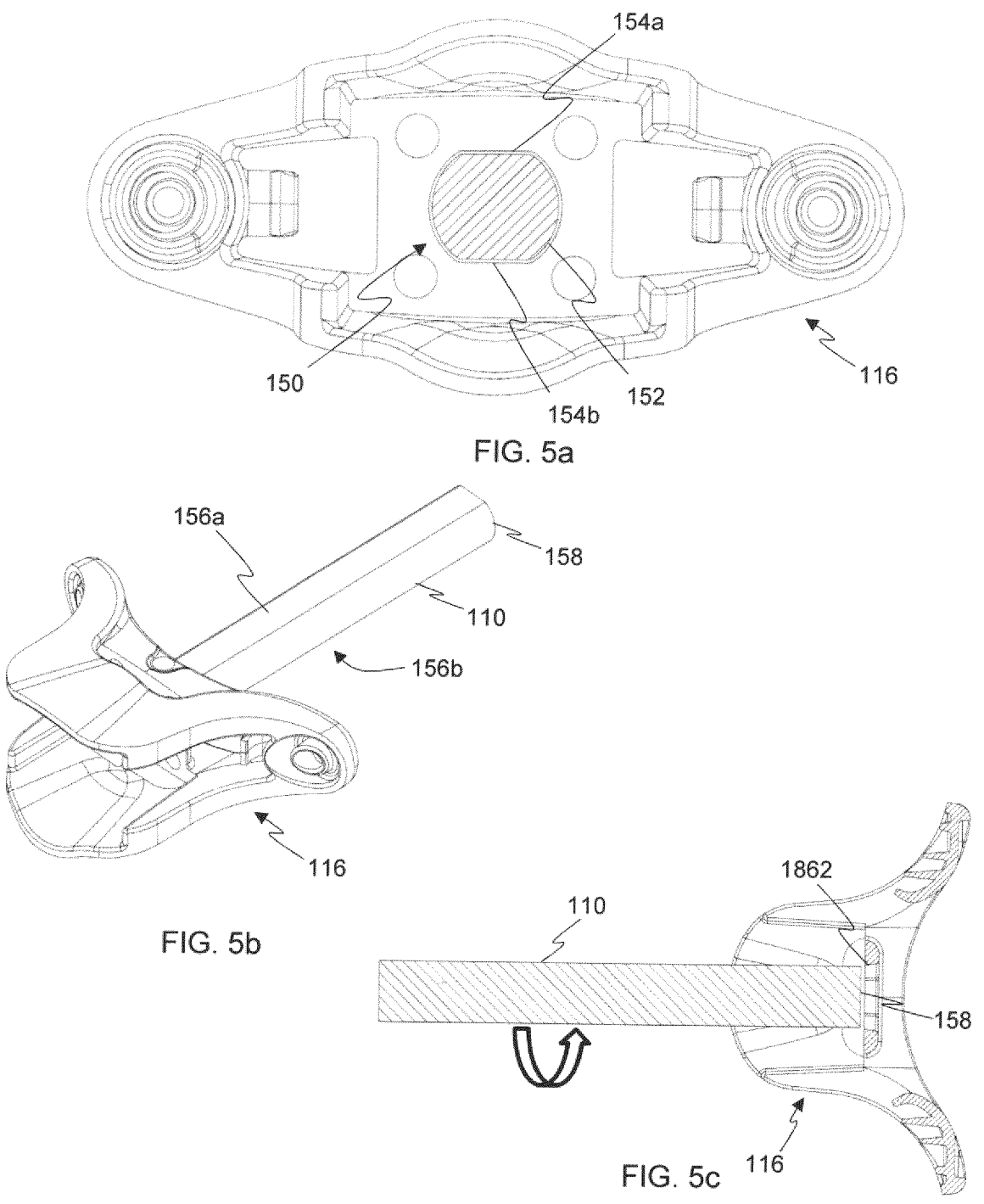
FIG. 5a is a plan view of a handle portion
FIG. 5b is an isometric view of a handle portion and a syringe plunger.
FIG. 5c is a section through a handle portion and a syringe plunger.

FIG. 5*a* shows an end elevation of the handle portion 116. FIG. 5*b* shows a perspective view of a syringe plunger 110 partially passed through the handle portion 116. FIG. 5*c* shows a section through a syringe plunger 110 fully passed through a handle portion 116. For clarity, FIGS. 5*a-c* do not show other features of the safety syringe 100.

In exemplary apparatus, the safety plunger 118 may be coupled to the syringe plunger 110 by preventing rotation of the syringe plunger 110 along at least part of its inward stroke. As rotation of the syringe plunger 110 is prevented, the syringe plunger 110 moves along its inward stroke under a force applied to the safety plunger 118 because the first and second screw threads 142, 144 cannot interact to rotate the syringe plunger 110. The syringe plunger 118 and the safety plunger 110 are therefore longitudinally coupled, as they move together on an inward (or outward) stroke.

In exemplary apparatus, the handle portion 116 may comprise a keyed aperture 152 in the handle portion 116. The keyed aperture 152 comprises keying features 154*a,b* that correspond to keying features 156*a,b* on the syringe plunger 110, such that rotation of the syringe plunger 110 is prevented when the keying features 156*a,b* of the syringe plunger 110 engage with the keying features 154*a,b* of the handle portion 116, as shown in FIG. 5*b*.

The syringe plunger 110 decouples from the safety plunger 118 when the syringe plunger 110 is released from the handle portion 116 and allowed to rotate. In exemplary apparatus, this may be provided by the keying features 156*a,b* of the syringe plunger 110 no longer engaging with the keying features 154*a,b* of the handle portion 116. For example, the syringe plunger 110 may comprise keying features 156*a,b* over only part of its length and once those keying features 156*a,b* have passed through the keyed aperture 152, the syringe plunger 110 may be free to rotate. Alternatively, and as shown in FIGS. 5*a-c*, a head 158 of the syringe plunger 110 may be configured such that it can pass through the keyed aperture 152. In exemplary syringe plungers 110, the head 158 may have the same cross section as the region of the syringe plunger 110 comprising the keying features 156*a,b*. In such exemplary cases, the syringe plunger 110 is configured to pass through the aperture 152 completely, as shown in FIG. 5*c*. When the syringe plunger 110 has passed through the keyed aperture 152, the keying features 156*a,b* of the syringe plunger 110 are no longer engaged with the keying features 154*a,b* of the keyed aperture 152 and the syringe plunger 110 is free to rotate. At this point, the syringe plunger 110 and the safety plunger 118 are longitudinally decoupled.

It is noted that the term "decoupled" as used herein encompasses any situation in which relative motion is permitted between a syringe plunger and a safety plunger. In specific apparatus, the relative motion may be relative longitudinal motion. This applies to all apparatus disclosed herein. That is, a syringe plunger does not need to be detached or separated from a safety plunger in order to be decoupled from it. Further, there may still be some movement of a safety plunger along its inward (or outward) stroke after decoupling, but there is a difference between a rate of movement between a safety plunger and a syringe plunger. For example, there may be some longitudinal movement of the syringe plunger along the inward stroke as well as rotational movement within the barrel after longitudinal decoupling, but the ratio of movement of the safety plunger and the syringe plunger is not 1:1.

The inventors have further appreciated that the use of, for example 2.25 ml and 3 ml syringes, can lead to problems associated with delivering more than 1 ml of drug to a patient during a single injection. In some cases, drug delivery of volumes greater than 1 ml into an injection site may lead to issues with the patient not absorbing the full dose. As such, some of the drug may leak from the injection site after the needle is removed.

Generally disclosed herein are safety syringes operable to alter or otherwise control the depth of a syringe needle within an injection site before the complete drug dose has been delivered. In exemplary arrangements this may involve a partial withdrawal of the syringe needle before the complete dose has been delivered. Exemplary safety syringes comprise a sheath and a syringe plunger configured to drive a bung within a syringe barrel to dispense a substance within the barrel. In exemplary safety syringes, the needle may be extracted from an injection site by a force applied to the site by the sheath as it is deployed. In some devices this is done after all of the drug within the barrel has been delivered. In exemplary arrangements disclosed herein, the sheath may be deployable at a point on the inward stroke before an end of the inward stroke, such that the sheath applies a force to the skin of the patient to extract the needle before the syringe plunger completely dispenses the drug.

The concept of sheath deployment (and therefore needle withdrawal) before a drug has been completely dispensed may be applied to many safety syringe arrangements. However, the specific arrangement described below is in reference to exemplary safety syringes previously described.

Exemplary safety syringes may operate in substantially the same way as described above but may be configured to longitudinally couple the safety plunger to the sheath before the syringe plunger has reached the end of its inward stroke. In exemplary arrangements, the sheath contact surfaces, which may be the ends of the safety plunger arms (see FIG. 3) or a surface rearward of the ends of the safety plunger arms (as shown in FIG. 2*b*) are positioned such that the safety plunger arms and the sheath are longitudinally coupled before the safety plunger and the syringe plunger are longitudinally decoupled. In such arrangements, the safety plunger, the syringe plunger and the sheath are longitudinally coupled together for part of the inward stroke of the safety plunger and therefore move forwards together. Further, a forward end of the sheath is positioned relative to a forward end of the neck of the barrel such that after longitudinal coupling of the safety plunger and the sheath, the forward end of the sheath is forward of the forward end of the neck of the barrel before the syringe plunger is at an innermost point on its inward stroke. This results in the forward end of the sheath contacting the injection site and partially withdrawing the needle before the drug within the barrel is fully delivered.

The inventors have appreciated that in exemplary safety syringes, a rotational force may be applied to the syringe plunger. For example, a rotational force may be imparted on the barrel by rotation of the syringe plunger (as described above) by the first and second threads after longitudinal decoupling of the safety plunger and the syringe plunger. In such safety syringes, it may be desirable to prevent the rotational force from causing rotation of the barrel itself.

Figure 6A:
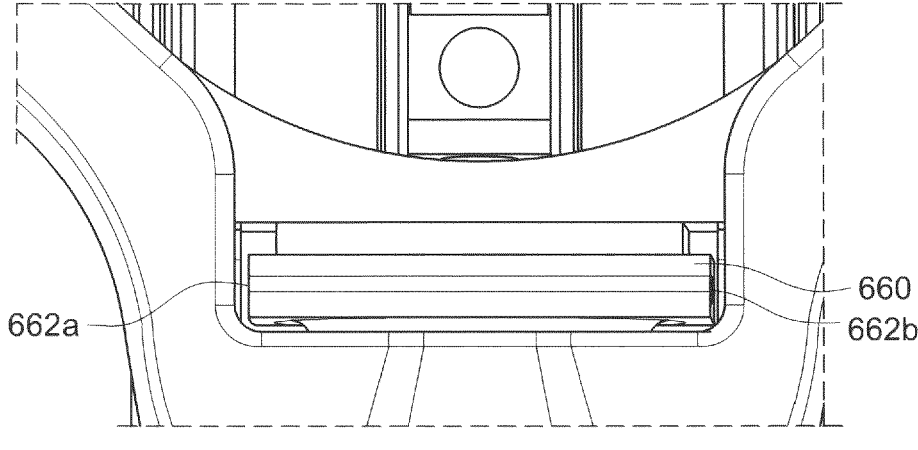
FIG. 6a is a plan view of a barrel of a syringe with a cropped flange.
Figure 6B:
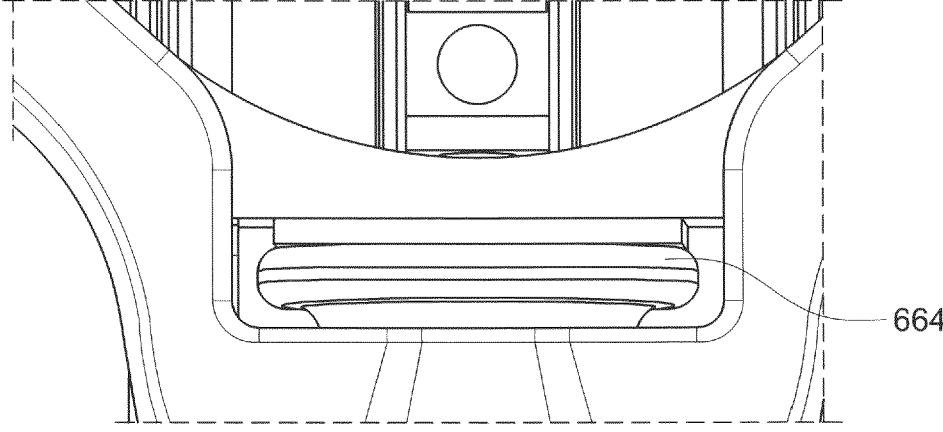
FIG. 6b is a plan view of a barrel of a syringe with a round flange

A number of barrel designs exist having a full flange, a cropped flange or no flange. FIG. 6*a* shows a barrel with a cropped flange 660 (with keying surfaces 662*a*, 662*b*) and FIG. 6*b* shows a barrel with a round flange 664. For syringe barrels with cropped flanges, keyed surfaces in an inner wall of the handle portion (within which the barrel is received) may be utilised to prevent rotation of the barrel. However, for syringe barrels with full (or round) flanges an alternative way of preventing rotation of the barrel may be needed. It will be understood however, that arrangements for preventing rotation described below may be utilised with substantially any barrel flange geometry (including cropped flanges).

Generally disclosed herein is a brake for use with a safety syringe apparatus, such as the safety syringe apparatus described above, and configured to provide a frictional force to resist a rotational force applied to a syringe barrel. The brake may be in contact with the barrel.

The brake may be configured to resist a rotational force applied to a rotationally stationary barrel. As such, the brake may increase static friction (or stiction) between the brake and the barrel that needs to be overcome to enable relative rotational movement between the brake and the barrel. By increasing the frictional forces the brake resists the barrel beginning to rotate.

Figure 7:
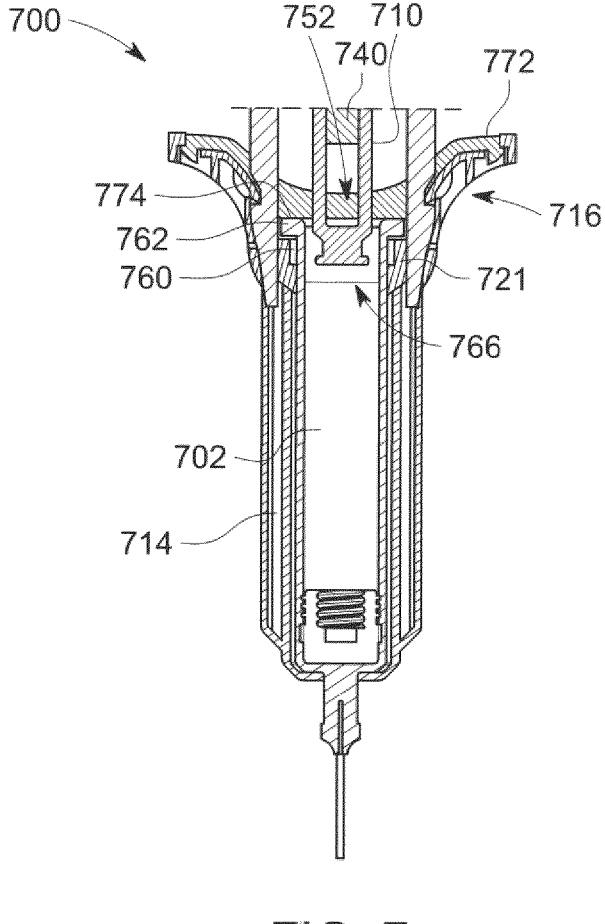
FIG. 7 is a section through a safety syringe.

FIG. 7 shows an exemplary safety syringe 700. Many of the features of the safety syringe 700 are the same or similar to the features of the exemplary safety syringes described above, and as such the same reference numbers are utilised for these features, except they begin with a '7'. Therefore not all of the features of the safety syringe 700 are described here to avoid repetition. The focus of the following description is on the features of the safety syringe that differ from features already described above.

The safety syringe 700 comprises a syringe comprising a barrel 702, a bung 712 and a syringe plunger 710. The safety syringe 700 may further comprise a safety syringe apparatus for use with the syringe. The safety syringe apparatus comprises a sheath 714, a handle portion 716, a safety plunger 718, a rotation mechanism 740 and a brake 760.

As described above, in exemplary safety syringes 700, the syringe plunger 710 may be configured to rotate within the barrel 702 after longitudinal decoupling from the safety plunger 714. Rotation of the syringe plunger 710 may be caused by the first and second threads as described above. Although not shown in FIG. 7, the syringe plunger 710 is engaged with the bung 712 during rotation as it will be at the end of its inward stroke. Further, the first and second threads on the safety plunger and the syringe plunger 710 respectively interact to force the syringe plunger 710 forwards relative to the bung 712 as well as rotating the syringe plunger 710. The bung 712 is restrained by the end of the barrel. This action causes friction between the syringe plunger 710 and the bung 712, which acts to transfer the rotational force on the syringe plunger 710 to the bung 712. As the bung 712 has an interference fit within the barrel, the rotational force is therefore transferred to the barrel. This rotational force may be resisted by the brake 760. Rotation of the barrel may thereby be prevented.

The brake 760 may be in contact with the barrel 702 directly. In the exemplary safety syringe 700 of FIG. 7, the brake 760 is in contact with a sidewall 721 of the barrel 702. In alternative arrangements, the brake 760 may be indirectly in contact with the barrel 702. For example, a collar (or other component) may be longitudinally and rotationally secured to the barrel 702 and the brake may contact the collar in order to resist rotation of the barrel 702.

In the exemplary safety syringe 700, the handle portion 716 is fixed longitudinally with respect to the barrel 702. The handle portion comprises an aperture within which the barrel 702 is received.

The handle portion 716 is further configured to receive the brake 760 and hold the brake 760 in compression against the barrel 702 when assembled. In the safety syringe 700 of FIG. 7, the brake 760 is held in compression directly against the barrel 702. In alternative arrangements the brake 760 may be held in compression against the barrel 702 indirectly, for example, the brake 760 may be held in compression against a further component that is coupled to the barrel.

In the safety syringe 700 shown in FIG. 7, a radial thickness of the brake may be slightly greater than the gap formed between the barrel 702 and the handle portion 716, when the barrel is received therein. As such, the brake 760 is held in compression between the barrel 702 and the handle portion 716 by an interference fit therebetween.

In the exemplary safety syringe 700, the brake comprises a grommet. The grommet may comprise a resiliently deformable material, such as a rubberised or an elastomer element in contact with the barrel. In FIG. 7, the elastomer element of the grommet is in direct contact with the barrel, however in alternative arrangements the elastomer element may be in indirect contact with the barrel 702 (via for example a further component coupled to the barrel).

The grommet comprises an aperture 766 configured to receive the barrel 702 of the syringe. The aperture 766 may be of slightly smaller dimensions than the outer dimensions of the barrel 702 such that an interference fit is formed between the grommet and the barrel 702. As such, the brake 760 may be formed by the inner circumference of the aperture 766. That is, the frictional forces to resist rotational movement of the barrel 702 applied by the bung 712, may be provided by the compressive force applied to the sidewall of barrel 702 by the grommet due to the interference fit. The material of the brake and the barrel may be configured to provide a high coefficient of friction to maximise the resistance of rotational movement of the barrel. For example, the brake may be manufactured from a thermoplastic elastomer, for example Dryflex® or Mediprene®.

FIGS. 8a-8f show sections through exemplary arrangements for implementation of the brake.

Figure 8A:
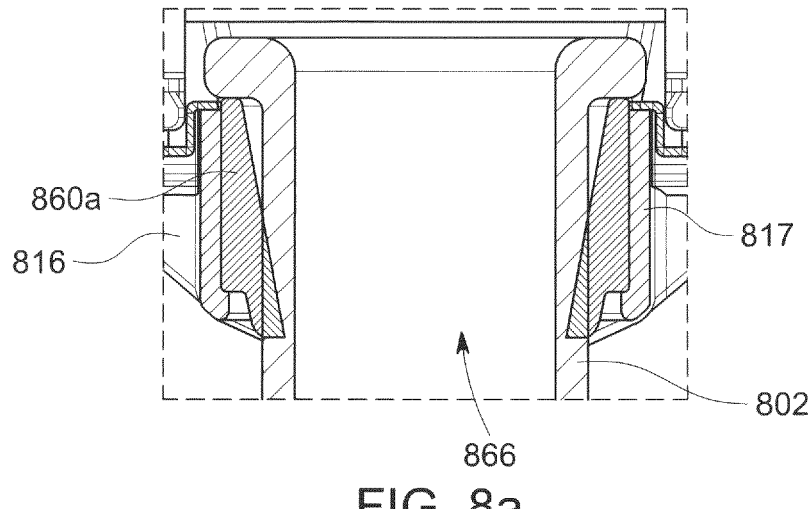

In FIG. 8a, the barrel 802 is shown within the aperture in the handle portion 816. The aperture is defined by the sidewall 817. The brake 860a comprises a grommet, which in this example is resiliently deformable. Inner sidewalls of the grommet 860a are angled inwards from a rear point forwards. That is, the inner sidewalls of the grommet 860a define a narrower and narrower aperture in a forward direction. As shown in FIG. 8a, a forward region of the inner sidewall of the grommet 860a meets the sidewall of the barrel 802. The brake is therefore engaged.

Figure 8B:
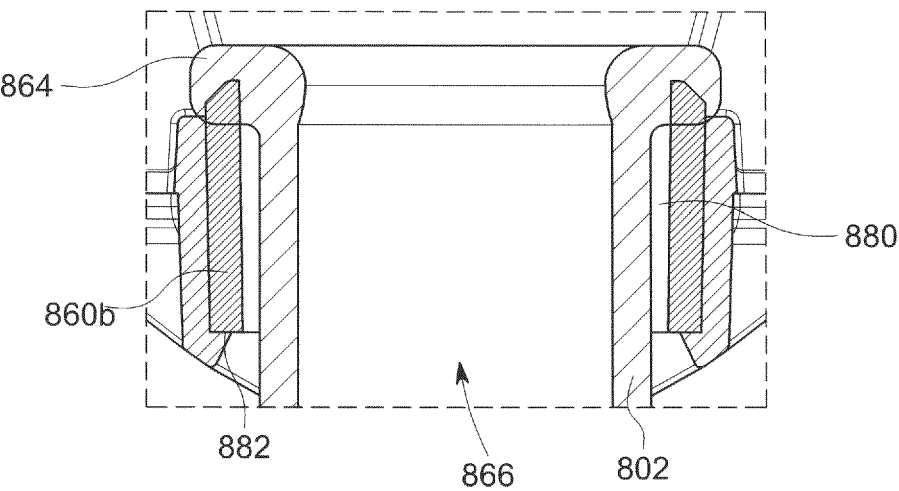

FIG. 8b shows a grommet 860b, which forms an aperture 866 having a diameter greater than an outer diameter of the barrel 802. The barrel 802 is therefore able to pass through the aperture 866 without interference from the grommet 860b. That is, the barrel 802 is able to pass through the aperture 866 without the sidewalls of the barrel 802 meeting the inner sidewalls of the grommet 860b. A clearance 880 exists between the sidewall of the barrel 802 and the grommet 860b. In this and other exemplary arrangements, the clearance may be up to 0.5 mm, up to 0.75 mm, up to 1 mm or up to 1.25 mm.

Therefore, as the barrel 802 enters the aperture 860b, the brake is not engaged. The brake is engaged after the barrel 802 has entered the aperture 866.

In the exemplary arrangement of FIG. 8b, the grommet 860b rests against a reaction surface 880. The reaction surface 882 resists forward motion of the grommet 860b. In FIG. 8a, the reaction surface is transverse to an axial direction of the safety syringe.

In this and other exemplary arrangements, the grommet 860b extends rearwards from a rear end of the aperture 866. That is, a rear portion of the grommet 860b stands proud of the aperture 866 formed in the handle portion. This allows the grommet 860b to interact with a flange 864 of the barrel 802. As the flange 864 meets the rear portion of the grommet 860b, a forward force is applied to the grommet 860b. The forward force is resisted by the reaction surface 882. The grommet 860b is compressed. Compression of the grommet 860b produces stiction between the grommet 860b and the flange 864. The brake is thereby engaged. Producing stiction between the grommet 860b and an underside of the flange 864 has the advantage that force applied by a user during use of the syringe increases the compression of the grommet 860b and therefore increases the stiction. For the avoidance of doubt, as used herein, the term "stiction" encompasses friction that tends to prevent stationary surfaces from being set in motion.

In addition to the stiction between the grommet 860b and the underside of the flange 864, the grommet 860b may also expand laterally under compression. An inner sidewall of the grommet 860b may therefore meet the sidewall of the barrel 802. Further stiction may therefore be produced against the sidewall of the barrel 802.

Figure 8C:
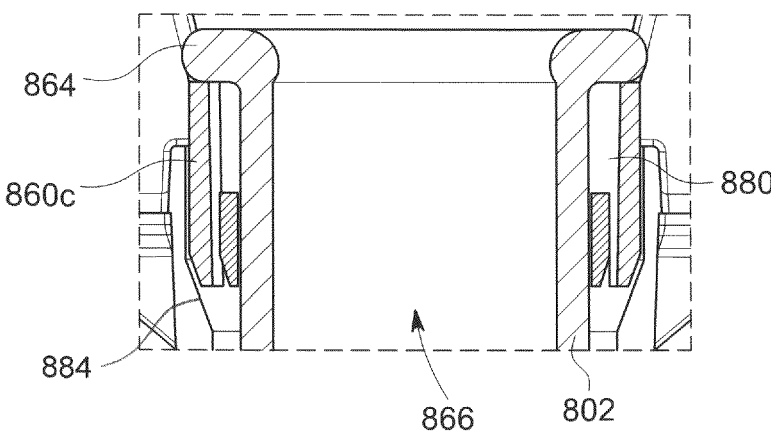

FIG. 8c also shows a grommet 860c, which forms an aperture 866 having a diameter greater than an outer diameter of the barrel 802. A similar clearance 880 to that in FIG. 8b is therefore formed and the brake is not engaged when the barrel 802 enters the aperture 866.

The arrangement of FIG. 8c also includes a reaction surface 884. The reaction surface 884 is angled radially inwards. On axial forward movement of the grommet 860c, the grommet 860c interacts with the reaction surface 884 and is guided radially inwards. The grommet 860c therefore meets the sidewall of the barrel 802, producing stiction. As with other exemplary arrangements, a rearward surface of the grommet 860c is configured to be contacted by the flange 864 of the barrel 802. Further movement of the barrel 802 in a forward direction produces a forward force on the grommet 860c. The grommet 860c interacts with the reaction surface 884 and is displaced laterally, in this case radially inwards. As with FIG. 8b, the grommet 860c may extend rearwards from the rear end of the aperture 866.

FIG. 8d shows an arrangement in which an insert 872 is fittable to the handle portion 816. The insert 872 may be fitted to the handle portion 816 after the barrel 802 has been received within the aperture 866. The insert 872 is configured to engage the brake. In exemplary arrangements, the insert 872 may engage the brake by compressing at least part of a grommet 860d against the barrel 802 to produce stiction.

In the example of FIG. 8d, the insert comprises at least one lateral displacement feature 886. The lateral displacement feature 886 may comprise a generally circular shape wall configured to extend into the handle portion 816 radially outside of the sidewall of the barrel 802, and, where a flange is present, the flange 864. The lateral displacement feature 886 may comprise a plurality of discrete sections of the generally circular shaped wall. The lateral displacement feature 886 may comprise any element extending into the handle portion 816 and configured to displace the grommet 860d laterally, for example, laterally inwards.

The grommet 860d is positioned within the aperture 866. A clearance 880 is provided between the inner sidewall of the grommet 860d and the barrel 802, as described above.

As the insert 872 is fitted to the handle portion 816, the lateral displacement feature 886 contacts the grommet 860d, displacing it radially inwards. The grommet 860d meets the sidewall of the barrel 802 and produces stiction. One or both of the lateral displacement feature 886 and the grommet may include a chamfered surface for lateral displacement of the grommet 860d radially inwards.

In some exemplary arrangements, the brake (e.g. grommet) may be fitted to the barrel 802 of the syringe to form a sub-assembly. The sub-assembly may then be fitted into the handle portion 816 such that it is axially and rotationally fixed relative to the handle portion 816. Further, in exemplary arrangements, the handle portion 816 may include a bottom out surface, against which the flange 864 of the barrel 802 will rest after the barrel 802 is fully inserted into the aperture 866. The bottom out surface prevents further forward motion of the barrel 802.

FIGS. 8e and 8f show exemplary arrangements in which the handle portion 816e, 816f is operable to open the aperture 866. By opening the aperture 866, the exemplary arrangements may increase the diameter of the aperture 866 to be greater than the diameter of the barrel 802. In other arrangements, such as those shown in FIGS. 8e and 8f, the aperture 866 is opened such that it is broken and the barrel 802 may be inserted laterally. After insertion of the barrel 802 (either laterally or through) into the aperture 866, the handle portion 816e, 816f is operable to close the aperture 866 around the barrel 802. The aperture 866 may comprise a grommet 860e, 860f. If the aperture 866 is opened such that the diameter is increased to greater than the diameter of the barrel 802, the grommet may be in a single piece. In the examples shown in FIGS. 8e and 8f, the aperture is broken and the grommet 860e, 860f is in a plurality of separate parts, in these cases, two parts.

The handle portion 816e, 816f in FIGS. 8e and 8f comprises two portions that are separable to open or break the aperture 866. The portions of the handle 816e are connected by a hinge and separable by opening the hinge, and the portions of handle portion 816f are separated fully. The aperture 866 is opened and the barrel 802 is inserted into the aperture 866. The aperture 866 is then closed, e.g. by closing the hinge or otherwise joining the portions of the handle portion 816e, 816f. The grommet 860e, 860f is pressed into contact with the sidewall of the barrel 802, thereby producing stiction and engaging the brake.

Figure 9:
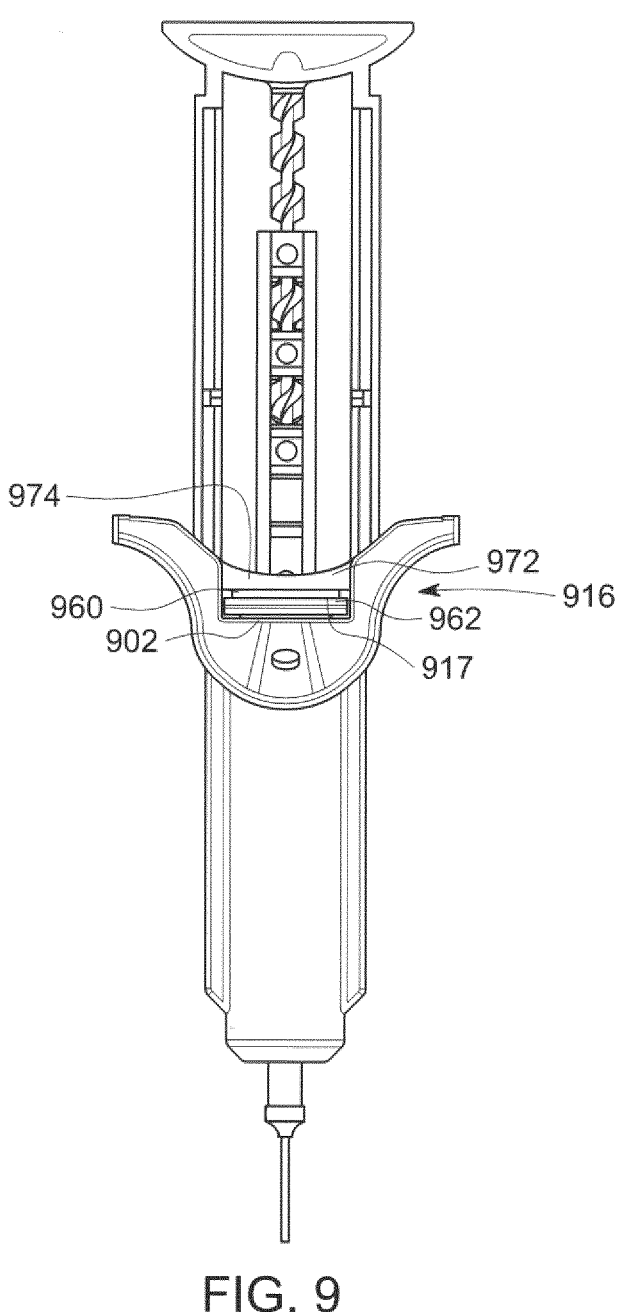
FIG. 9 is a plan view of a safety syringe.

A further arrangement is shown in FIG. 9. Many of the features of the safety syringe 900 of FIG. 9 are the same or similar to the features of the exemplary safety syringes described above, and as such the same reference numbers are utilised for these features, except they begin with a '9'. Therefore not all of the features of the safety syringe 900 are described here to avoid repetition. The focus of the following description is on the features of the safety syringe that differ from features already described above.

As shown in FIG. 9, the brake 960 may contact a top (or rear) surface 917 of the barrel 902. The barrel 902 may be held within the handle portion 916 such that the top surface 917 of the barrel 902 holds the brake 960 in compression. The brake 960 may again comprise a grommet.

In this alternative arrangement the safety syringe 900 may further comprise an insert 972 fitted to the handle portion 916. In such an arrangement, the safety syringe apparatus may be assembled by inserting the syringe (and the brake 960) into the aperture (not shown in FIG. 9) of the handle portion 916 from the rear side of the handle portion 916 such that the needle-end of the syringe passes through the handle aperture first. The insert 972 may then be fitted to the rear side of the handle portion 916 over the inserted syringe. For example, the insert 972 may be configured to snap-fit to the rear side of the handle portion 916.

The insert 972 may be configured to hold the brake 960 in compression against the top surface of the barrel 917. The gap formed between a forward surface 974 of the insert and the top surface 917 of the barrel 902 when the insert 972 is fitted to the handle is of slightly smaller dimension than the thickness of the brake 960 in the longitudinal direction. As such, the frictional forces to resist rotational movement of the barrel 902 may be provided by the force applied to the top of barrel as a result of the compression of the brake 960 between the barrel 902 and the insert 972.

In the arrangement shown in FIG. 9, the insert 972 may hold the brake 960 in compression against a flange 962 of the barrel 902. It will be appreciated however that in alternative arrangements, the barrel 902 may not have a flange. In such an arrangement, the gap formed between a forward surface 974 of the insert 972 and the flange 962 (or the top of the barrel in arrangements without flanges), when the insert 972 is fitted to the handle portion 916, is of slightly smaller dimensions than a longitudinal thickness of the brake 960 when the brake 960 is inserted.

Shown best in FIG. 7, the insert 772, 972 may comprise a keyed aperture 752 (see FIG. 7) corresponding to keying features on the syringe plunger 710 and configured to prevent rotation until decoupling as described above in respect of the safety syringe 100. As such, the insert 772, 972 may be utilised with either brake arrangement previously described. Alternatively the insert 772, 972 may be utilised in isolation from the brake 760, 960 and with barrels comprising round flanges.

The skilled person will appreciate that the above exemplary arrangements are exemplary only and should not be considered limiting on the scope of the invention, which is defined in the appended claims.

The invention claimed is:
1. A safety syringe comprising:
a barrel having an opening at an end thereof;
a bung positioned in the barrel and creating a volume between the opening and the bung;
a handle portion, having an aperture, secured to the barrel;

a syringe plunger slidably engaged with the handle portion and moveable within the barrel on an inward stroke to drive the bung forwards within the barrel to cause a substance within the volume to be expelled from the opening;

a rotation mechanism configured to rotate the syringe plunger within the barrel at a point during the inward stroke when the syringe plunger is in contact with the bung, such that a rotational force is applied to the barrel; and a brake comprising a compressible material connected to the handle portion and configured to provide a frictional force to resist the rotational force applied to the barrel wherein the handle portion is configured to hold the compressible material of the brake in compression directly against an outer portion of the barrel, wherein the brake is an elastomeric grommet arranged around a sidewall of the barrel;

wherein an inner diameter of the elastomeric grommet is larger than an outer diameter of the sidewall of the barrel;

wherein the grommet rests against a reaction surface at a forward end of the grommet, wherein the reaction surface is transverse to an axial direction of the safety syringe; and wherein a portion of the grommet stands proud of the aperture, extends longitudinally away from the aperture in a rearward direction, and is configured to interact with a flange of the barrel and the handle portion to engage the brake by compression of the portion of the grommet standing proud of the aperture between the flange of the barrel and the handle portion, wherein a clearance exists between the sidewall of the barrel and an inner sidewall of the grommet during insertion of the barrel into the handle portion.

2. The safety syringe according to claim 1, wherein the brake forms at least part of the aperture in the handle portion in which the barrel is received.

3. The safety syringe according to claim 2, wherein the brake forms at least part of an inner circumference of the aperture.

4. The safety syringe according to claim 2, wherein the barrel is received within the aperture such that an interference fit is formed between the barrel and the brake.

5. The safety syringe according to claim 4, wherein before the barrel is received within the aperture, a diameter of the aperture is greater than a diameter of the barrel of the syringe, and wherein the brake is engageable upon receipt of the barrel within the aperture.

6. The safety syringe according to claim 5, wherein the handle portion is operable to open the aperture, and is further operable to close the aperture after insertion of the barrel within the aperture to engage the brake wherein the handle portion comprises two portions, separable to open the aperture wherein the two portions are connected by a hinge.

7. The safety syringe according to claim 1, wherein the handle portion comprises the reaction surface which is configured to compress and/or laterally move the grommet on application of an axial force on the grommet with respect to the handle portion wherein the reaction surface is angled to displace the grommet laterally inwards on axial movement of the grommet with respect to the handle portion wherein the reaction surface is configured to resist axial movement of the grommet with respect to the handle portion, such that the axial force on the grommet compresses and/or laterally expands the grommet.

8. The safety syringe according to claim 7, wherein a rearward surface of the grommet is configured to contact a flange of the barrel when the barrel is received in the aperture wherein the rearward surface extends from a rearward end of the aperture.

9. The safety syringe according to claim 8, wherein the handle portion comprises a bottom out face configured to contact the flange of the barrel upon receipt of the barrel within the aperture for preventing forward movement of the barrel.

10. The safety syringe according to claim 1, further comprising an insert fittable to the handle portion and configured to engage the brake.

11. The safety syringe according to claim 10, wherein the insert comprises one or more lateral displacement features configured to interact with the grommet to displace the grommet laterally inwards.

12. The safety syringe according to claim 10, wherein the brake is in contact with a rearward surface of the barrel.

13. The safety syringe according to claim 12, wherein the insert is configured to hold the brake in compression against the rearward surface of the barrel.

14. The safety syringe according to claim 1, further comprising:

a safety plunger longitudinally coupled to the syringe plunger such that an inward stroke of the safety plunger causes the inward stroke of the syringe plunger; and a sheath directly or indirectly slidably engaged with the handle portion and configured to cover at least partially the opening in the barrel, wherein the safety plunger is configured to longitudinally couple to the sheath at a first point on the inward stroke and is configured to longitudinally decouple from the syringe plunger at a second point on the inward stroke such that the safety plunger is longitudinally moveable independently of the syringe plunger, and wherein further movement of the safety plunger after longitudinally decoupling causes the sheath to at least partially cover the opening in the barrel wherein, prior to operation of the safety syringe, the safety plunger is longitudinally decoupled from the sheath and configured to longitudinally couple to the sheath at the first point on the inward stroke wherein the rotational force is applied to the barrel after longitudinal decoupling of the safety plunger and the syringe plunger wherein the rotation mechanism comprises a first screw thread on the safety plunger and a second screw thread on the syringe plunger and configured to engaged with the first screw thread to rotate the syringe plunger on movement of the safety plunger after longitudinal decoupling wherein the rotation mechanism is further configured to control a rate of travel of the safety plunger after longitudinal decoupling.

15. The safety syringe of claim 1, wherein the reaction surface is a first reaction surface, and wherein an outer sidewall of the grommet rests against a second reaction surface, transverse to the first reaction surface, inhibiting radially outward movement of the grommet, such that the grommet is configured to contact the sidewall of the barrel.

16. A safety syringe apparatus for use with a syringe comprising a barrel having an opening at an end thereof and a bung positioned in the barrel and creating a volume between the opening and the bung, the syringe apparatus comprising:

a handle portion, having an aperture, for securing to the barrel;

a syringe plunger slidably engaged with the handle portion and configured, when the handle portion is secured to the barrel, to be moveable within the barrel on an inward stroke to drive the bung forwards within the barrel to cause a substance within the volume to be expelled from the opening;

a rotation mechanism configured to rotate the syringe plunger within the barrel at a point during the inward stroke when the syringe plunger is in contact with the bung, such that a rotational force is applied to the barrel; and a brake comprising a compressible material connected to the handle portion and configured to provide a frictional force to resist the rotational force applied to the barrel, wherein the handle portion is configured to hold the compressible material of the brake in compression directly against an outer portion of the barrel, where the brake is an elastomeric grommet arranged around the barrel;

wherein the brake is an elastomeric grommet arranged around a sidewall of the barrel;

wherein an inner diameter of the elastomeric grommet is larger than an outer diameter of the sidewall of the barrel;

wherein the grommet rests against a reaction surface at a forward end of the grommet, wherein the reaction surface is transverse to an axial direction of the safety syringe;

wherein a portion of the grommet stands proud of the aperture, extends longitudinally away from the aperture in a rearward direction, and is configured to interact with a flange of the barrel and the handle portion to engage the brake by compression of the portion of the grommet standing proud of the aperture between the flange of the barrel and the handle portion; and wherein a clearance exists between the sidewall of the barrel and an inner sidewall of the grommet during insertion of the barrel into the handle portion.

17. A kit of parts for forming a safety syringe apparatus for use with a syringe comprising a barrel having an opening at an end thereof and a bung positioned in the barrel and creating a volume between the opening and the bung, the kit of parts comprising:

a handle portion, having an aperture, for securing to the barrel;

a syringe plunger for slidable engagement with the handle portion and configured, when the handle portion is secured to the barrel, to be moveable within the barrel on an inward stroke to drive the bung forwards within the barrel to cause a substance within the volume to be expelled from the opening;

a rotation mechanism configured to rotate the syringe plunger within the barrel at a point during the inward stroke when the syringe plunger is in contact with the bung, such that a rotational force is applied to the barrel; and a brake comprising a compressible material connectable to the handle portion and configured to provide a frictional force to resist the rotational force applied to the barrel wherein the handle portion is configured, when secured to the barrel, to hold the compressible material of the brake in compression directly against an outer portion of the barrel, where the brake is an elastomeric grommet arranged around the barrel wherein the brake is an elastomeric grommet arranged around a sidewall of the barrel;

wherein an inner diameter of the elastomeric grommet is larger than an outer diameter of the sidewall of the barrel;

wherein the grommet rests against a reaction surface at a forward end of the grommet, wherein the reaction surface is transverse to an axial direction of the safety syringe;

wherein a portion of the grommet stands proud of the aperture, extends longitudinally away from the aperture in a rearward direction, and is configured to interact with a flange of the barrel and the handle portion to engage the brake by compression of the portion of the grommet standing proud of the aperture between the flange of the barrel and the handle portion; and wherein a clearance exists between the sidewall of the barrel and an inner sidewall of the grommet during insertion of the barrel into the handle portion.

18. The kit of parts according to claim 17, further comprising:

a safety plunger configured to be longitudinally coupled to the syringe plunger such that an inward stroke of the safety plunger causes the inward stroke of the syringe plunger; and a sheath configured to cover at least partially the opening in the barrel, wherein the safety plunger is configured to longitudinally couple to the sheath at a first point on the inward stroke and is configured to longitudinally decouple from the syringe plunger at a second point on the inward stroke such that the safety plunger is longitudinally moveable independently of the syringe plunger, and wherein further movement of the safety plunger after longitudinal decoupling causes the sheath to at least partially cover the opening in the barrel.

* * * * *